United States Patent
Brama

(10) Patent No.: US 10,726,098 B2
(45) Date of Patent: Jul. 28, 2020

(54) METHOD, SYSTEM AND PROGRAM PRODUCT FOR TRANSFERRING GENETIC AND HEALTH DATA

(71) Applicant: Dror Samuel Brama, Jerusalem (IL)

(72) Inventor: Dror Samuel Brama, Jerusalem (IL)

(*) Notice: Subject to any disclaimer, the term of this patent is extended or adjusted under 35 U.S.C. 154(b) by 488 days.

(21) Appl. No.: 14/218,865

(22) Filed: Mar. 18, 2014

(65) Prior Publication Data
US 2015/0205929 A1 Jul. 23, 2015

Related U.S. Application Data

(60) Provisional application No. 61/930,850, filed on Jan. 23, 2014.

(51) Int. Cl.
G06F 19/00 (2018.01)
G06Q 20/06 (2012.01)
G16H 10/60 (2018.01)

(52) U.S. Cl.
CPC ....... *G06F 19/3418* (2013.01); *G06Q 20/065* (2013.01); *G16H 10/60* (2018.01)

(58) Field of Classification Search
CPC ..... G06F 19/34; G06F 19/3418; G16H 10/60; G06Q 20/065
USPC ....................................................... 705/2–3
See application file for complete search history.

(56) References Cited

U.S. PATENT DOCUMENTS

| | | | | |
|---|---|---|---|---|
| 8,316,237 B1* | 11/2012 | Felsher | ................. | H04L 9/0825 380/282 |
| 8,595,028 B2 | 11/2013 | Green, III et al. | | |
| 2003/0097561 A1* | 5/2003 | Wheeler | ................. | G06Q 20/02 713/168 |
| 2007/0192140 A1* | 8/2007 | Gropper | ................. | G06Q 50/24 705/3 |
| 2012/0123924 A1* | 5/2012 | Rose | .................... | G06Q 20/381 705/35 |
| 2012/0191703 A1* | 7/2012 | Huff | ..................... | G06Q 10/063 707/722 |
| 2015/0052009 A1* | 2/2015 | Ketchell, III | .......... | G06Q 50/22 705/26.8 |
| 2015/0363481 A1* | 12/2015 | Haynes | ............. | G06F 17/30595 707/748 |
| 2015/0379510 A1* | 12/2015 | Smith | ................. | G06Q 20/3829 705/71 |
| 2016/0085955 A1* | 3/2016 | Lerner | .................... | G06F 21/31 726/20 |

FOREIGN PATENT DOCUMENTS

| WO | WO 2001/050214 | 7/2001 |
|---|---|---|
| WO | WO 2013/070895 | 5/2013 |

* cited by examiner

*Primary Examiner* — Jason S Tiedeman
*Assistant Examiner* — Rachel F Durnin
(74) *Attorney, Agent, or Firm* — Blueshift IP, LLC; Robert Plotkin

(57) ABSTRACT

A method, system and program product comprise accessing a system having a digital currency infrastructure. At least one user address is created. Genetic and health related user data is prepared. The user data is transferred to the system wherein the system links the user data and the user address.

23 Claims, 6 Drawing Sheets

METHOD, SYSTEM AND PROGRAM PRODUCT FOR TRANSFERRING GENETIC AND HEALTH DATA

CROSS-REFERENCE TO RELATED APPLICATIONS

The present Utility patent application claims priority benefit of the U.S. provisional application for patent Ser. No. 61/930,850 entitled "Platform for exchange of medical and genetical data over Crypto Currencies peer to peer platforms (Digital Currencies)", filed on Jan. 23, 2014 under 35 U.S.C. 119(e). The contents of this related provisional application are incorporated herein by reference for all purposes to the extent that such subject matter is not inconsistent herewith or limiting hereof.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the invention generally relate to data transfers. More particularly, the invention relates to data transfers emphasizing security and privacy.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Many fields of research may suffer from concerns about security and/or privacy. In a non-limiting example, genetic medical research may have difficulty collecting large sets of data, correlating clinical data with genetic data, and providing ease of access and incentives due to concerns over security and/or privacy.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. One such aspect of the prior art shows a method and system for an information collector to collect information from information suppliers and provide an incentive for the information suppliers to provide the information. By way of educational background, another aspect of the prior art generally useful to be aware of provides a computer program product for assembling a database comprising electronic medical records. Another such aspect of the prior art relates to systems and methods of utilizing the data captured in an integrated medical software system to conduct medical research, to maintain disease registries, to analyze the quality and safety of healthcare providers, and to conduct composite clinical and financial analytics. However, these solutions may be unable alleviate concerns of security and privacy of data. A solution which did and also could provide incentive for people to share data and give researchers easy and validated access to the data would be desirable.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
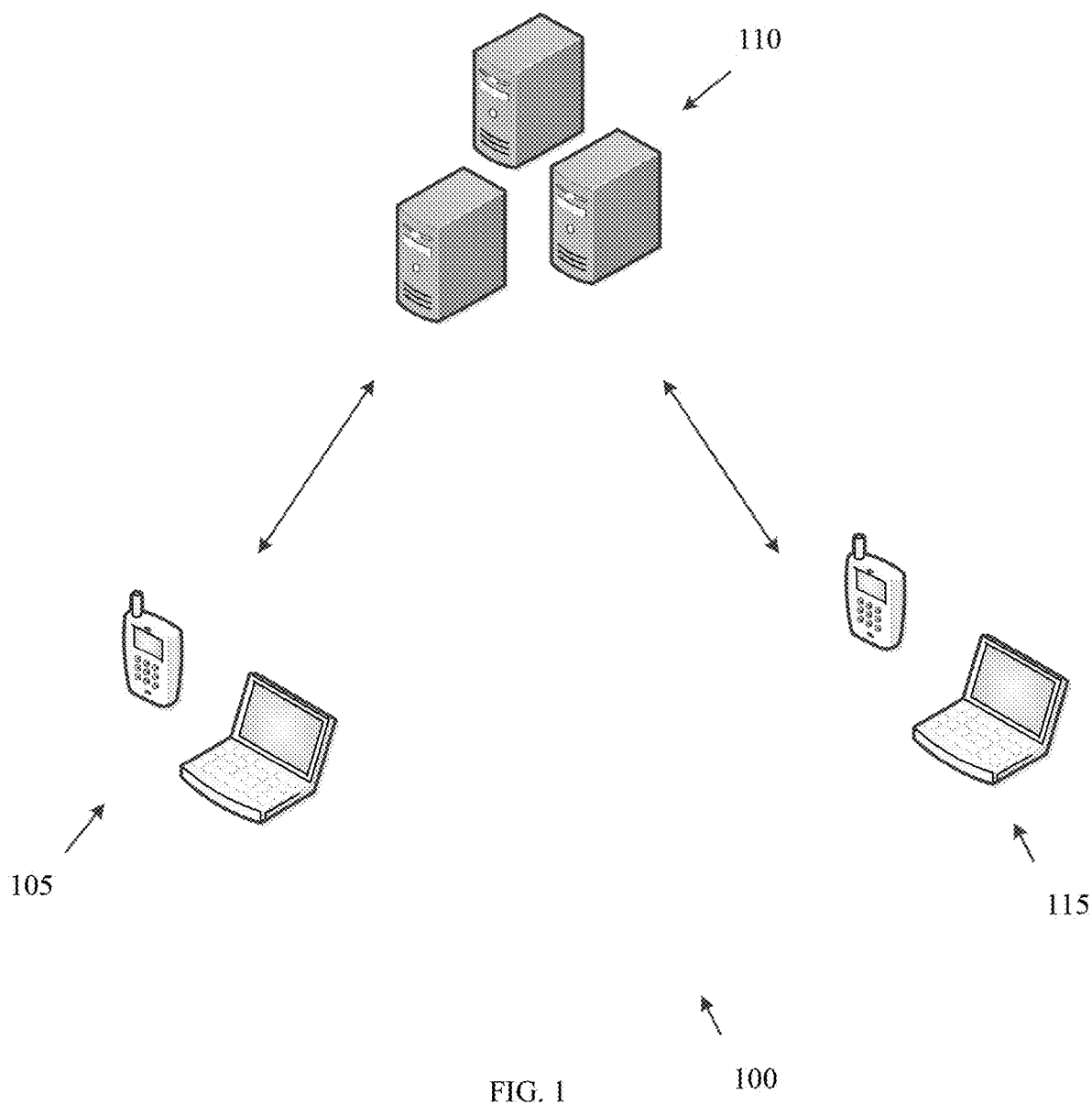
FIG. 1 is an illustration of an exemplary system for facilitating data transfers between parties, in accordance with an embodiment of the present invention.

Unless otherwise indicated illustrations in the figures are not necessarily drawn to scale.

DETAILED DESCRIPTION OF SOME EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present application or of any further application derived therefrom.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

Headings provided herein are for convenience and are not to be taken as limiting the disclosure in any way.

The enumerated listing of items does not imply that any or all of the items are mutually exclusive, unless expressly specified otherwise.

The terms "a", "an" and "the" mean "one or more", unless expressly specified otherwise.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

A "computer" may refer to one or more apparatus and/or one or more systems that are capable of accepting a structured input, processing the structured input according to prescribed rules, and producing results of the processing as output. Examples of a computer may include: a computer; a stationary and/or portable computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a client; an interactive television; a web appliance; a telecommunications device with internet access; a hybrid combination of a computer and an interactive television; a portable computer; a tablet personal computer (PC); a personal digital assistant (PDA); a portable telephone; application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, a system on a chip, or a chip set; a data acquisition device; an optical computer; a quantum computer; a biological computer; and generally, an apparatus that may accept data, process data according to one or more stored software programs, generate results, and typically include input, output, storage, arithmetic, logic, and control units.

Those of skill in the art will appreciate that where appropriate, some embodiments of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Where appropriate, embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

"Software" may refer to prescribed rules to operate a computer. Examples of software may include: code segments in one or more computer-readable languages; graphical and or/textual instructions; applets; pre-compiled code; interpreted code; compiled code; and computer programs.

The example embodiments described herein can be implemented in an operating environment comprising computer-executable instructions (e.g., software) installed on a computer, in hardware, or in a combination of software and hardware. The computer-executable instructions can be written in a computer programming language or can be embodied in firmware logic. If written in a programming language conforming to a recognized standard, such instructions can be executed on a variety of hardware platforms and for interfaces to a variety of operating systems. Although not limited thereto, computer software program code for carrying out operations for aspects of the present invention can be written in any combination of one or more suitable programming languages, including an object oriented programming languages and/or conventional procedural programming languages, and/or programming languages such as, for example, Hyper text Markup Language (HTML), Dynamic HTML, Extensible Markup Language (XML), Extensible Stylesheet Language (XSL), Document Style Semantics and Specification Language (DSSSL), Cascading Style Sheets (CSS), Synchronized Multimedia Integration Language (SMIL), Wireless Markup Language (WML), Java™, Jini™, C, C++, Smalltalk, Perl, UNIX Shell, Visual Basic or Visual Basic Script, Virtual Reality Markup Language (VRML), ColdFusion™, Scrypt, or other compilers, assemblers, interpreters or other computer languages or platforms.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

A network is a collection of links and nodes (e.g., multiple computers and/or other devices connected together) arranged so that information may be passed from one part of the network to another over multiple links and through various nodes. Examples of networks include the Internet, the public switched telephone network, the global Telex network, computer networks (e.g., an intranet, an extranet, a local-area network, or a wide-area network), wired networks, and wireless networks.

The Internet is a worldwide network of computers and computer networks arranged to allow the easy and robust exchange of information between computer users. Hundreds of millions of people around the world have access to computers connected to the Internet via Internet Service Providers (ISPs). Content providers (e.g., website owners or operators) place multimedia information (e.g., text, graphics, audio, video, animation, and other forms of data) at specific locations on the Internet referred to as webpages. Websites comprise a collection of connected, or otherwise related, webpages. The combination of all the websites and their corresponding webpages on the Internet is generally known as the World Wide Web (WWW) or simply the Web.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The flowchart and block diagrams in the figures illustrate the architecture, functionality, and operation of possible implementations of systems, methods and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

Further, although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

It will be readily apparent that the various methods and algorithms described herein may be implemented by, e.g., appropriately programmed general purpose computers and computing devices. Typically a processor (e.g., a microprocessor) will receive instructions from a memory or like device, and execute those instructions, thereby performing a process defined by those instructions. Further, programs that implement such methods and algorithms may be stored and transmitted using a variety of known media.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The functionality and/or the features of a device may be alternatively embodied by one or more other devices which are not explicitly described as having such functionality/features. Thus, other embodiments of the present invention need not include the device itself.

The term "computer-readable medium" as used herein refers to any medium that participates in providing data (e.g., instructions) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave as described hereinafter, or any other medium from which a computer can read.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols, such as Bluetooth, TDMA, CDMA, 3G.

Where databases are described, it will be understood by one of ordinary skill in the art that (i) alternative database structures to those described may be readily employed, (ii) other memory structures besides databases may be readily employed. Any schematic illustrations and accompanying descriptions of any sample databases presented herein are exemplary arrangements for stored representations of information. Any number of other arrangements may be employed besides those suggested by the tables shown. Similarly, any illustrated entries of the databases represent exemplary information only; those skilled in the art will understand that the number and content of the entries can be different from those illustrated herein. Further, despite any depiction of the databases as tables, an object-based model could be used to store and manipulate the data types of the present invention and likewise, object methods or behaviors can be used to implement the processes of the present invention.

A "computer system" may refer to a system having one or more computers, where each computer may include a computer-readable medium embodying software to operate the computer or one or more of its components. Examples of a computer system may include: a distributed computer system for processing information via computer systems linked by a network; two or more computer systems connected together via a network for transmitting and/or receiving information between the computer systems; a computer system including two or more processors within a single computer; and one or more apparatuses and/or one or more systems that may accept data, may process data in accordance with one or more stored software programs, may generate results, and typically may include input, output, storage, arithmetic, logic, and control units.

A "network" may refer to a number of computers and associated devices that may be connected by communication facilities. A network may involve permanent connections such as cables or temporary connections such as those made through telephone or other communication links. A network may further include hard-wired connections (e.g., coaxial cable, twisted pair, optical fiber, waveguides, etc.) and/or wireless connections (e.g., radio frequency waveforms, free-space optical waveforms, acoustic waveforms, etc.). Examples of a network may include: an internet, such as the Internet; an intranet; a local area network (LAN); a wide area network (WAN); and a combination of networks, such as an internet and an intranet.

As used herein, the "client-side" application should be broadly construed to refer to an application, a page associated with that application, or some other resource or function invoked by a client-side request to the application. A "browser" as used herein is not intended to refer to any specific browser (e.g., Internet Explorer, Safari, FireFox, or the like), but should be broadly construed to refer to any client-side rendering engine that can access and display Internet-accessible resources. A "rich" client typically refers to a non-HTTP based client-side application, such as an SSH or CFIS client. Further, while typically the client-server interactions occur using HTTP, this is not a limitation either. The client server interaction may be formatted to conform to the Simple Object Access Protocol (SOAP) and travel over HTTP (over the public Internet), FTP, or any other reliable transport mechanism (such as IBM® MQSeries® technologies and CORBA, for transport over an enterprise intranet) may be used. Any application or functionality described herein may be implemented as native code, by providing hooks into another application, by facilitating use of the mechanism as a plug-in, by linking to the mechanism, and the like.

Exemplary networks may operate with any of a number of protocols, such as Internet protocol (IP), asynchronous transfer mode (ATM), and/or synchronous optical network (SONET), user datagram protocol (UDP), IEEE 802.x, etc.

Embodiments of the present invention may include apparatuses for performing the operations disclosed herein. An apparatus may be specially constructed for the desired purposes, or it may comprise a general-purpose device selectively activated or reconfigured by a program stored in the device.

Embodiments of the invention may also be implemented in one or a combination of hardware, firmware, and software. They may be implemented as instructions stored on a machine-readable medium, which may be read and executed by a computing platform to perform the operations described herein.

More specifically, as will be appreciated by one skilled in the art, aspects of the present invention may be embodied as a system, method or computer program product. Accordingly, aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

In the following description and claims, the terms "computer program medium" and "computer readable medium" may be used to generally refer to media such as, but not limited to, removable storage drives, a hard disk installed in hard disk drive, and the like. These computer program products may provide software to a computer system. Embodiments of the invention may be directed to such computer program products.

An algorithm is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

Unless specifically stated otherwise, and as may be apparent from the following description and claims, it should be appreciated that throughout the specification descriptions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments within the scope of the present disclosure may also include tangible and/or non-transitory computer-readable storage media for carrying or having computer-executable instructions or data structures stored thereon. Such non-transitory computer-readable storage media can be any available media that can be accessed by a general purpose or special purpose computer, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be used to carry or store desired program code means in the form of computer-executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

While a non-transitory computer readable medium includes, but is not limited to, a hard drive, compact disc, flash memory, volatile memory, random access memory, magnetic memory, optical memory, semiconductor based memory, phase change memory, optical memory, periodically refreshed memory, and the like; the non-transitory computer readable medium, however, does not include a pure transitory signal per se; i.e., where the medium itself is transitory.

Some embodiments of the present invention may provide means and/or method for providing security and/or privacy of shared data. Some of these embodiments may also provide means and/or methods for effective transferring of data and/or communication between parties.

FIG. 1 is an illustration of an exemplary system for facilitating data transfers between parties, in accordance with an embodiment of the present invention. In the present embodiment, a first user may use an electronic device 105 to communicate bi-directionally with one or more servers or nodes in a peer to peer system 110. In some embodiments, servers or nodes in a peer to peer system may store and/or manage various types of information including, without limitation, user-provided data and pointers to locations of data. In the present embodiment, servers or nodes in a peer to peer system 110 may communicate bi-directionally with other electronic devices 115 to facilitate communication between multiple users. In some embodiments, servers or nodes in a peer to peer system 110 may be suitable for matching sets of data. In a non-limiting example, a first set of data may be a pointer to a location of a second set of data. In some embodiments, some sets of data may be publicly viewable and others may have restricted access.

Figure 2:
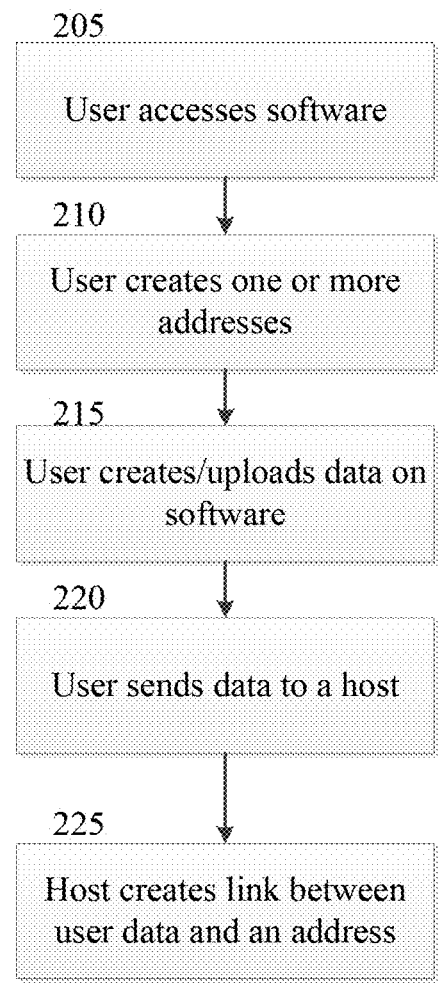
FIG. 2 is an illustration of an exemplary method for making data available to other users, in accordance with an embodiment of the present invention.

FIG. 2 is an illustration of an exemplary method for making data available to other users, in accordance with an embodiment of the present invention. In the present embodiment, a user may access embodiment software in a step 205. In some embodiments, software may be suitable for storing data and/or managing transfers of data using an internet service. In some of these embodiments, software may reside on a user device 105. In other embodiments, software may reside on an external server 110. In a non-limiting example, software may be similar in functionality to a QT bitcoin open source wallet, or other digital wallet implementations. In some embodiments, software may be suitable for pairing sets of data. In some of these embodiments, some data sets may be public and some may be private. In a non-limiting example, in many digital decentralized currencies, there is the existence of a public ledger of transactions. In peer to peer setups, each peer may verify the validity of the ledger (block chain) mathematically. Every block chain is based on Merkle Tree structure, so every node (block of transactions) may be validated by the wallet software. In most centralized systems, the block chain needs to be public, or exposed to the wallets. Since every wallet has access to the block chain, a function may be created that may find a specific transaction, or sort the transactions according to types. In at least one embodiment, software may have a variety of functions, including, without limitation, sending and/or receiving transactions, verifying peer-to-peer protocols, sending and/or receiving digitally signed messages, an verifying sources. In the present embodiment, a user may use software to create one or more addresses in a step 210. In some embodiments, an address may be a set of data which may be used for identification purposes. In a non-limiting example, a method for address creation of the public side of the private\public key pair may be as follows:

Version=1 byte of 0 (zero); on the test network, this is 1 byte of 111
Key hash=Version concatenated with RIPEMD-160(SHA-256(public key))
Checksum=1st 4 bytes of SHA-256(SHA-256(Key hash))
Address=Base58Encode(Key hash concatenated with Checksum)
The typical result may look like this:
2cf24dba5fb0a30e26e83b2ac5b9e29e1b161e5c1fa7425e73043362938b9824 (first round is sha-256)
b6a9c8c230722b7c748331a8b450f05566dc7d0f (with ripemd-160).

In many embodiments, addresses may mask a user's identity. In some embodiments, a user may have addresses which may serve differing functions. In a non-limiting example, a user may use a first address primarily for sending personal data and a second address primarily for receiving data from other users. In some embodiments, a user may create and/or upload data on software in a step 215. In other embodiments, the user may send the data to the host and just title the data with his address, so in this option no additional data will be created in the wallet. In some embodiments, data may be in any form, including, without limitation, text, images, video, audio samples, etc. In a non-limiting example, data may be a user's genetic data, i.e. a full raw sequencing of an entire genome, a prototyping of SNPs, or a partial set of both. In some embodiments, users may encrypt data. In at least one embodiment, a user may provide identifying information to a data sample, including, without limitation, a title. In some embodiments, the user may simply put his "address" as the title for the data. In some embodiments, the user may give the data a unique address, and have a special transaction recorded on the block chain from his address to that unique address of the data. The user may take a unique subset of data from his data and hash it to be the public address of this data (as a non-limiting example, taking a unique portion of his DNA and hashing it). In the present embodiment, a user may send data to a host in a step 220. In some embodiments, a host may use a server 110 or other system suitable for storing and/or managing data. In a non-limiting example, a host may be a business entity which may have capacity to host computer readable data and/or query computer readable data. In the present non-limiting example, the host may interact with users through users' public addresses and may also host a mixing service and/or public elements of a system, i.e. public transactions log, directories for addresses sorted by classifications, and other public aggregates of data. In one or more embodiments, a host may know a user's address but not a user's identity. In the present embodiment, the host may create a link between user data and a user address in a step 225. In some embodiments, host may send a public transaction to user address with a reference to user's data to create a link. In some embodiments, this step may also be initiated by the user where the user may create the link between his address and the hosted data. In some of these embodiments, reference may be a message embedded in a transaction which may serve as a pointer to location of user data. In a non-limiting example, there are 2 ways of expressing data. The first is the transaction itself. The fact that a public logged transaction happened between two addresses, is expressing a link between those addresses. If one of the addresses is known to represent something, like a published address of a data host, then anything else but the existence of the transaction may not be needed. The second way is embedding a short message within the transaction, which may tell further info or pointers.

In some embodiments, a user and/or a host may encrypt data. In some of these embodiments, encrypted data may require a user to perform a special transaction in order to access data.

Figure 3:
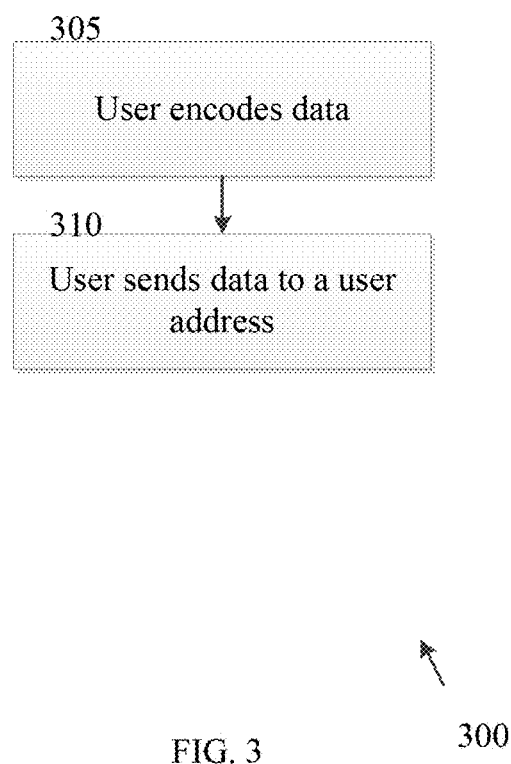
FIG. 3 is an illustration of an exemplary method for transfers of data between parties, in accordance with an embodiment of the present invention.

FIG. 3 is an illustration of an exemplary method for transfers of data between parties, in accordance with an embodiment of the present invention. In the present embodiment, a user may encode data in a step 305. In a non-limiting example, a user may be a doctor and data may be sensitive medical data. In the present embodiment, the doctor may encode the medical data to common classification terms, i.e. SNOMED. In the present embodiment, a user may send data or a pointer to a user address in a step 310. In some embodiments, software may record transactions between a user and a user's address on a public ledger/block chain. In a non-limiting example, a doctor may send medical data to a user's address. In the present non-limiting example, the doctor may know a user's address which may serve as user's receiving address. Further, in the present non-limiting example, user may have one or more other addresses, i.e. for uploading personal data, which doctor may not know is associated to user's receiving address. In some embodiments, data transferred between users may be associated with other data. In a non-limiting example, a doctor may send medical data to a patient and may embed with the data a message with a reference to a location of further data, i.e. imaging, background, lab results, etc.

In some embodiments, software may have further features to provide increased anonymity. In some of these embodiments, software may use a mixing service which may implement various rules. In a non-limiting example, an exemplary rule may be that each transaction to a given address may be forwarded to a second address to provide that a connection between sender and recipient may be diluted.

Figure 4:
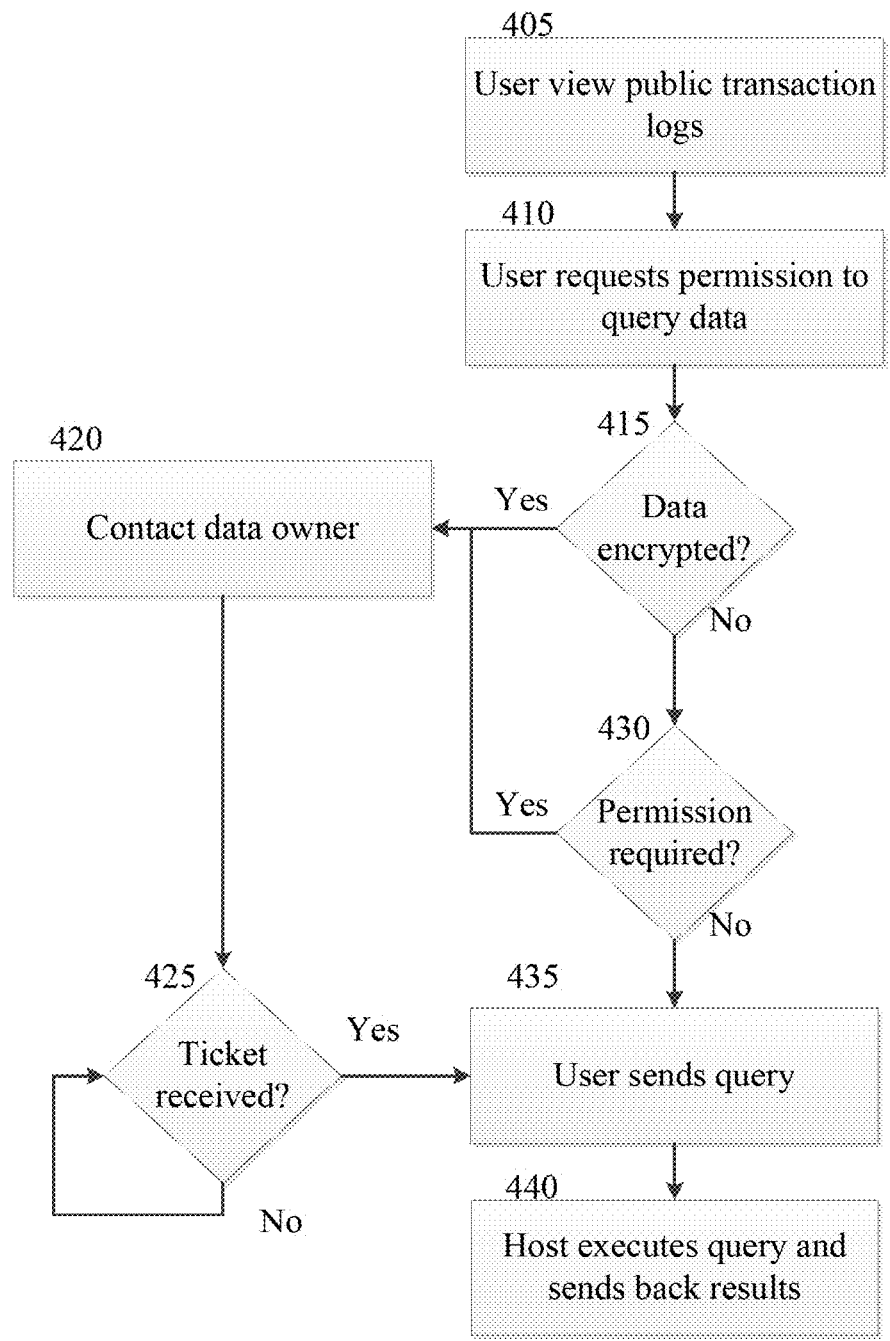
FIG. 4 is an illustration of an exemplary method for searching for sets of data, in accordance with an embodiment of the present invention.

FIG. 4 is an illustration of an exemplary method for searching for sets of data, in accordance with an embodiment of the present invention. In the present embodiment, a user may view publicly available transaction logs in a step 405. In some embodiments, transactions may be created from interactions between users and/or between a user and a host. In many embodiments, transaction logs may have addresses associated of user or users involved in transaction. In some embodiments, transaction logs may have identifying information which users may effectively search through to find desired data. In a non-limiting example, there are currently three known ways of embedding small pieces of data in the "block chain" transactions log. In the financial system, the intention is to carry data such as invoice number, contract reference, and they serve similar purpose as the short comment texts available in bank wire transfers. The first method is transacting very small amount in the same transaction, which is forwarded to a different known address that is used as a marker. The second is using the internal messaging built into the transaction protocols of some digital currencies. The third is by using a payment protocol, which holds reference to set of rules to be fulfilled as part of the transaction.

In the present embodiment, user may request permission to query desired data from a host of desired data in a step 410. In some embodiments, user may contact host directly. In other embodiments, user may contact host through another entity. In a non-limiting example, a user may contact a host through a "market maker" which may hold services required for various operations of parties. In the present embodiment, system may determine whether desired data is encrypted in a step 415. In some embodiments, users and/or hosts may encrypt data. In the present embodiment, if data is encrypted, host may require user to acquire a "ticket" from owner of data. In some embodiments, a ticket may be a special transaction from a data owner which provides permission to use data owner's data. In the present embodiment, user may contact data owner in a step 420. In some embodiments, user may use data owner's address to contact data owner. In the present embodiment, system may determine whether user has received a ticket in a step 425. In some embodiments, system may search for existence of relevant transaction between user and data owner to determine whether ticket has been received. In other embodiments, user and/or data owner may contact system to show ticket has been received. In a non-limiting example, the block chain is public. Once a "ticket transaction" is recorded the host knows that a ticket is issued, without knowing the user—just seeing this special transaction coming from his address. In the present embodiment, system may determine whether permission is required to use data owner's data in a step 430. If permission is required then the user may contact data owner in the step 420 to obtain a ticket. In the present embodiment, if user has received relevant ticket, user may then query host for desired data in a step 435. Further, in the present embodiment, host may execute query and send back results in a step 440.

In some embodiments, users may use software to pay other users. In some of these embodiments, users may make payments using, without limitation, digital coins, shares in revenue based on data received, performance of services, etc. In a non-limiting example, the payment may be a transaction of, but not limited to, digital coins, like bitcoin, or a voucher or some IOU unit redeemable in other payment system, online or offline, In a non-limiting example, a user of a data owner's data may pay data owner following or before accessing data. In a non-limiting example, if the user fails to pay the data owner, the block chain system has a built-in feature that may enable enforcement. There may be an option to limit the ability of spending the input of a certain address (basically—limiting the ability to withdraw its balance) by requiring a machine-verifiable set of instructions, such as, but not limited to, multi signature. When a need to enforce a contract is required, a condition may be set on a property, which requires a signature from agreed third party to release the property. This works for current enforcement of contracts. For contracts on future unknown revenues, a trusted third party may be used. In a non-limiting example, a medical company contracts users to use their data, and promise to pay them 20% of the revenues from the derived results. The "Market Maker" will hold—by legal agreement—part of the IP rights in the derived results. If it is determined that the company is in breach of its contract, it may enforce the contract legally.

In many embodiments, a market maker may serve a variety of functions, including, without limitation, holding a public ledger (block chain) of addresses and/or transactions, enabling searching and/or sorting services on transactions, holding a bidding and/or matching services to connect users with other users and/or hosts, automating contact between parties, and distributing messages and/or payments.

In some embodiments, users may encode ancestry relationships (parents, children, siblings) as transactions from an address to address.

Some embodiments may be an "app" or "template" for a digital wallet for downloading from an "app store" for block chain or digital wallets. Some embodiments may be a client side digital wallet with the features embedded. Some embodiments may be a web hosted digital wallet that users log in to. Some embodiments may be an add-on for medical management systems available in healthcare services, hospital etc. Some embodiments may be an add-on to genetic data extraction software used to extract, store and analyze genetic data. Some embodiment may be an add-on to medical records warehouse software used by hospital and healthcare systems.

Some embodiments of the present invention may be used in a variety of ways. In a non-limiting example, a doctor or healthcare provided who may be updating a client's medical record may access software to have an option to encode client's record as a transaction to client's digital wallet address. In the present embodiment, if client agrees, software may encode a reference in a block chain. Further, in the present embodiment, transactions may be signed by known address of healthcare organization so that validity of reference may be assured. In another non-limiting example, a health insurer, or government public health system holding medical records, may register to a service which may enable clients to expose data for research. In the present non-limiting example, healthcare organization may offer incentives to clients i.e. discounts, knowledge, extended cover, share in profits, etc. Further, in the present non-limiting example, if user agrees, a public address may be generated which may be a target to such encoded transactions. In still another non-limiting example, a website with bidding and/or automated contract capability may approach holders of medical and genetic data and may offer them an option to register in research bids. In the present non-limiting example, if holders agree, website may enable them to register their user records as public addresses and have an ability to encode references to data in public viewable transactions. Further, in the present non-limiting example, website may offer researchers to bid on use of data, and, if bids accepted, website may facilitate automated contacts between parties, including, without limitation, getting user permission, server-side decryption of data, sending query results to researcher, and distributing messages or shares back to data holder or owners.

Those skilled in the art will readily recognize, in light of and in accordance with the teachings of the present invention, that any of the foregoing steps and/or system modules may be suitably replaced, reordered, removed and additional steps and/or system modules may be inserted depending upon the needs of the particular application, and that the systems of the foregoing embodiments may be implemented using any of a wide variety of suitable processes and system modules, and is not limited to any particular computer hardware, software, middleware, firmware, microcode and the like. For any method steps described in the present application that can be carried out on a computing machine, a typical computer system can, when appropriately configured or designed, serve as a computer system in which those aspects of the invention may be embodied.

Figure 5:
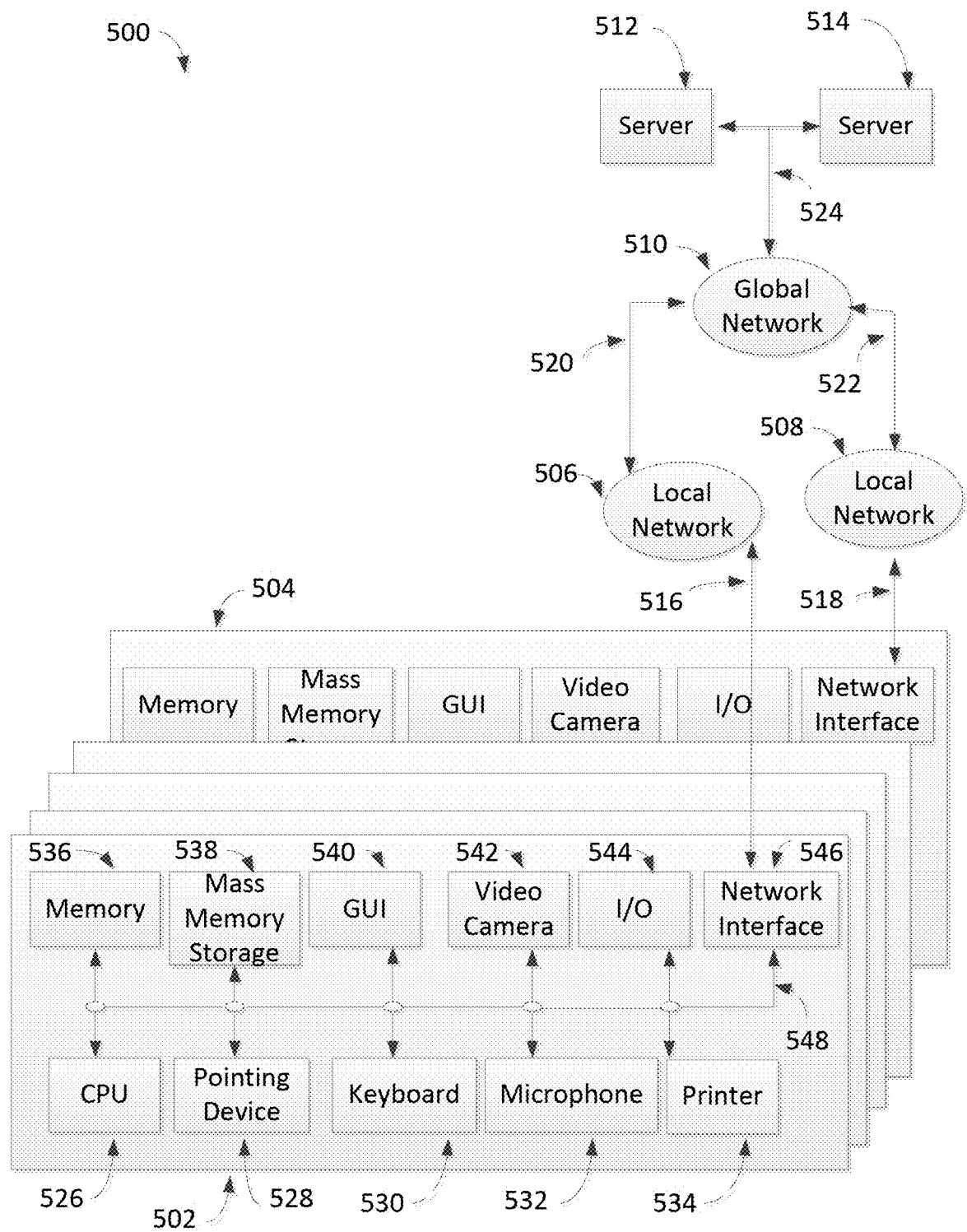
FIG. 5 is a block diagram depicting an exemplary client/server system which may be used by an exemplary web-enabled/networked embodiment of the present invention.

FIG. 5 is a block diagram depicting an exemplary client/server system which may be used by an exemplary web-enabled/networked embodiment of the present invention.

A communication system 500 includes a multiplicity of clients with a sampling of clients denoted as a client 502 and a client 504, a multiplicity of local networks with a sampling of networks denoted as a local network 506 and a local network 508, a global network 510 and a multiplicity of servers with a sampling of servers denoted as a server 512 and a server 514.

Client 502 may communicate bi-directionally with local network 506 via a communication channel 516. Client 504 may communicate bi-directionally with local network 508 via a communication channel 518. Local network 506 may communicate bi-directionally with global network 510 via a communication channel 520. Local network 508 may communicate bi-directionally with global network 510 via a communication channel 522. Global network 510 may communicate bi-directionally with server 512 and server 514 via a communication channel 524. Server 512 and server 514 may communicate bi-directionally with each other via a communication channel 524. Furthermore, clients 502, 504, local networks 506, 508, global network 510 and servers 512, 514 may each communicate bi-directionally with each other.

In one embodiment, global network 510 may operate as the Internet. It will be understood by those skilled in the art that communication system 500 may take many different forms. Non-limiting examples of forms for communication system 500 include local area networks (LANs), wide area networks (WANs), wired telephone networks, wireless networks, or any other network supporting data communication between respective entities.

Clients 502 and 504 may take many different forms. Non-limiting examples of clients 502 and 504 include personal computers, personal digital assistants (PDAs), cellular phones and smartphones.

Client 502 includes a CPU 526, a pointing device 528, a keyboard 530, a microphone 532, a printer 534, a memory 536, a mass memory storage 538, a GUI 540, a video camera 542, an input/output interface 544 and a network interface 546.

CPU 526, pointing device 528, keyboard 530, microphone 532, printer 534, memory 536, mass memory storage 538, GUI 540, video camera 542, input/output interface 544 and network interface 546 may communicate in a unidirectional manner or a bi-directional manner with each other via a communication channel 548. Communication channel 548 may be configured as a single communication channel or a multiplicity of communication channels.

CPU 526 may be comprised of a single processor or multiple processors. CPU 526 may be of various types including micro-controllers (e.g., with embedded RAM/ROM) and microprocessors such as programmable devices (e.g., RISC or SISC based, or CPLDs and FPGAs) and devices not capable of being programmed such as gate array ASICs (Application Specific Integrated Circuits) or general purpose microprocessors.

As is well known in the art, memory 536 is used typically to transfer data and instructions to CPU 526 in a bi-directional manner. Memory 536, as discussed previously, may include any suitable computer-readable media, intended for data storage, such as those described above excluding any wired or wireless transmissions unless specifically noted. Mass memory storage 538 may also be coupled bi-directionally to CPU 526 and provides additional data storage capacity and may include any of the computer-readable media described above. Mass memory storage 538 may be used to store programs, data and the like and is typically a secondary storage medium such as a hard disk. It will be appreciated that the information retained within mass memory storage 538, may, in appropriate cases, be incorporated in standard fashion as part of memory 536 as virtual memory.

CPU 526 may be coupled to GUI 540. GUI 540 enables a user to view the operation of computer operating system and software. CPU 526 may be coupled to pointing device 528. Non-limiting examples of pointing device 528 include computer mouse, trackball and touchpad. Pointing device 528 enables a user with the capability to maneuver a computer cursor about the viewing area of GUI 540 and select areas or features in the viewing area of GUI 540. CPU 526 may be coupled to keyboard 530. Keyboard 530 enables a user with the capability to input alphanumeric textual information to CPU 526. CPU 526 may be coupled to microphone 532. Microphone 532 enables audio produced by a user to be recorded, processed and communicated by CPU 526. CPU 526 may be connected to printer 534. Printer 534 enables a user with the capability to print information to a sheet of paper. CPU 526 may be connected to video camera 542. Video camera 542 enables video produced or captured by user to be recorded, processed and communicated by CPU 526.

CPU 526 may also be coupled to input/output interface 544 that connects to one or more input/output devices such as such as CD-ROM, video monitors, track balls, mice, keyboards, microphones, touch-sensitive displays, transducer card readers, magnetic or paper tape readers, tablets, styluses, voice or handwriting recognizers, or other well-known input devices such as, of course, other computers.

Finally, CPU 526 optionally may be coupled to network interface 546 which enables communication with an external device such as a database or a computer or telecommunications or internet network using an external connection shown generally as communication channel 516, which may be implemented as a hardwired or wireless communications link using suitable conventional technologies. With such a connection, CPU 526 might receive information from the network, or might output information to a network in the course of performing the method steps described in the teachings of the present invention.

Figure 6:
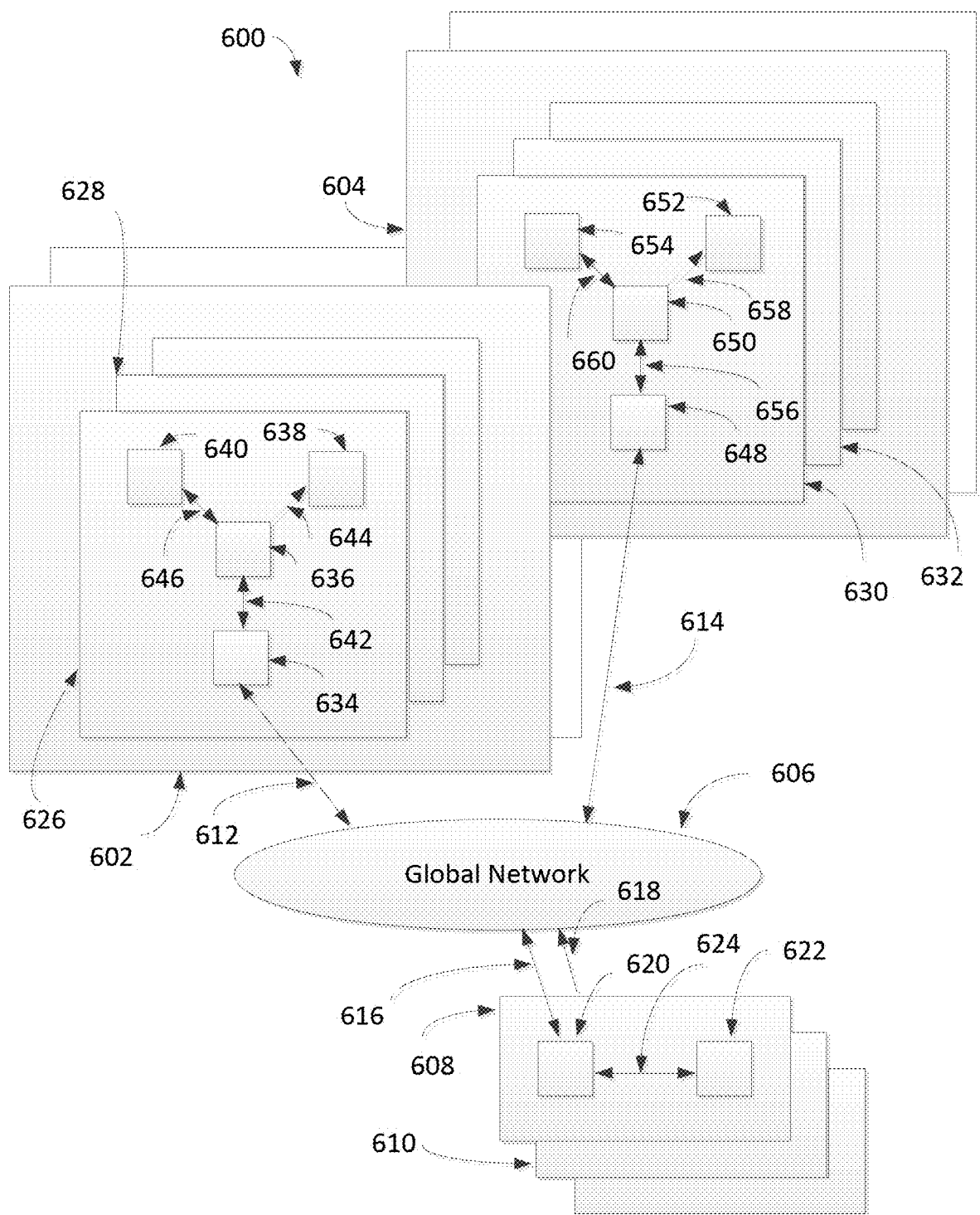
FIG. 6 illustrates a block diagram depicting a conventional client/server communication system.

FIG. 6 illustrates a block diagram depicting a conventional client/server communication system.

A communication system 600 includes a multiplicity of networked regions with a sampling of regions denoted as a network region 602 and a network region 604, a global network 606 and a multiplicity of servers with a sampling of servers denoted as a server device 608 and a server device 610.

Network region 602 and network region 604 may operate to represent a network contained within a geographical area or region. Non-limiting examples of representations for the geographical areas for the networked regions may include postal zip codes, telephone area codes, states, counties, cities and countries. Elements within network region 602 and 604 may operate to communicate with external elements within other networked regions or within elements contained within the same network region.

In some implementations, global network 606 may operate as the Internet. It will be understood by those skilled in the art that communication system 600 may take many different forms. Non-limiting examples of forms for communication system 600 include local area networks (LANs), wide area networks (WANs), wired telephone networks, cellular telephone networks or any other network supporting data communication between respective entities via hardwired or wireless communication networks. Global network 606 may operate to transfer information between the various networked elements.

Server device 608 and server device 610 may operate to execute software instructions, store information, support database operations and communicate with other networked elements. Non-limiting examples of software and scripting languages which may be executed on server device 608 and server device 610 include C, C++, C# and Java.

Network region 602 may operate to communicate bi-directionally with global network 606 via a communication channel 612. Network region 604 may operate to communicate bi-directionally with global network 606 via a communication channel 614. Server device 608 may operate to communicate bi-directionally with global network 606 via a communication channel 616. Server device 610 may operate to communicate bi-directionally with global network 606 via a communication channel 618. Network region 602 and 604, global network 606 and server devices 608 and 610 may operate to communicate with each other and with every other networked device located within communication system 600.

Server device 608 includes a networking device 620 and a server 622. Networking device 620 may operate to communicate bi-directionally with global network 606 via communication channel 616 and with server 622 via a communication channel 624. Server 622 may operate to execute software instructions and store information.

Network region 602 includes a multiplicity of clients with a sampling denoted as a client 626 and a client 628. Client 626 includes a networking device 634, a processor 636, a GUI 638 and an interface device 640. Non-limiting examples of devices for GUI 638 include monitors, televisions, cellular telephones, smartphones and PDAs (Personal Digital Assistants). Non-limiting examples of interface device 640 include pointing device, mouse, trackball, scanner and printer. Networking device 634 may communicate bi-directionally with global network 606 via communication channel 612 and with processor 636 via a communication channel 642. GUI 638 may receive information from processor 636 via a communication channel 644 for presentation to a user for viewing. Interface device 640 may operate to send control information to processor 636 and to receive information from processor 636 via a communication channel 646. Network region 604 includes a multiplicity of clients with a sampling denoted as a client 630 and a client 632. Client 630 includes a networking device 648, a processor 650, a GUI 652 and an interface device 654. Non-limiting examples of devices for GUI 638 include monitors, televisions, cellular telephones, smartphones and PDAs (Personal Digital Assistants). Non-limiting examples of interface device 640 include pointing devices, mousse, trackballs, scanners and printers. Networking device 648 may communicate bi-directionally with global network 606 via communication channel 614 and with processor 650 via a communication channel 656. GUI 652 may receive information from processor 650 via a communication channel 658 for presentation to a user for viewing. Interface device 654 may operate to send control information to processor 650 and to receive information from processor 650 via a communication channel 660.

For example, consider the case where a user interfacing with client 626 may want to execute a networked application. A user may enter the IP (Internet Protocol) address for the networked application using interface device 640. The IP address information may be communicated to processor 636 via communication channel 646. Processor 636 may then communicate the IP address information to networking device 634 via communication channel 642. Networking device 634 may then communicate the IP address information to global network 606 via communication channel 612. Global network 606 may then communicate the IP address information to networking device 620 of server device 608 via communication channel 616. Networking device 620 may then communicate the IP address information to server 622 via communication channel 624. Server 622 may receive the IP address information and after processing the IP address information may communicate return information to networking device 620 via communication channel 624. Networking device 620 may communicate the return information to global network 606 via communication channel 616. Global network 606 may communicate the return information to networking device 634 via communication channel 612. Networking device 634 may communicate the return information to processor 636 via communication channel 642. Processor 636 may communicate the return information to GUI 638 via communication channel 644. User may then view the return information on GUI 638.

It will be further apparent to those skilled in the art that at least a portion of the novel method steps and/or system components of the present invention may be practiced and/or located in location(s) possibly outside the jurisdiction of the United States of America (USA), whereby it will be accordingly readily recognized that at least a subset of the novel method steps and/or system components in the foregoing embodiments must be practiced within the jurisdiction of the USA for the benefit of an entity therein or to achieve an object of the present invention. Thus, some alternate embodiments of the present invention may be configured to comprise a smaller subset of the foregoing means for and/or steps described that the applications designer will selectively decide, depending upon the practical considerations of the particular implementation, to carry out and/or locate within the jurisdiction of the USA. For example, any of the foregoing described method steps and/or system components which may be performed remotely over a network (e.g., without limitation, a remotely located server) may be performed and/or located outside of the jurisdiction of the USA while the remaining method steps and/or system components (e.g., without limitation, a locally located client) of the forgoing embodiments are typically required to be located/performed in the USA for practical considerations. In client-server architectures, a remotely located server typically generates and transmits required information to a US based client, for use according to the teachings of the present invention. Depending upon the needs of the particular application, it will be readily apparent to those skilled in the art, in light of the teachings of the present invention, which aspects of the present invention can or should be located locally and which can or should be located remotely. Thus, for any claims construction of the following claim limitations that are construed under 35 USC § 112 (6) it is intended that the corresponding means for and/or steps for carrying out the claimed function are the ones that are locally implemented within the jurisdiction of the USA, while the remaining aspect(s) performed or located remotely outside the USA are not intended to be construed under 35 USC § 112 (6). In some embodiments, the methods and/or system components which may be located and/or performed remotely include, without limitation, nodes of a peer to peer system.

It is noted that according to USA law, all claims must be set forth as a coherent, cooperating set of limitations that work in functional combination to achieve a useful result as a whole. Accordingly, for any claim having functional limitations interpreted under 35 USC § 112 (6) where the embodiment in question is implemented as a client-server system with a remote server located outside of the USA, each such recited function is intended to mean the function of combining, in a logical manner, the information of that claim limitation with at least one other limitation of the claim. For example, in client-server systems where certain information claimed under 35 USC § 112 (6) is/(are) dependent on one or more remote servers located outside the USA, it is intended that each such recited function under 35 USC § 112 (6) is to be interpreted as the function of the local system receiving the remotely generated information required by a locally implemented claim limitation, wherein the structures and or steps which enable, and breath life into the expression of such functions claimed under 35 USC § 112 (6) are the corresponding steps and/or means located within the jurisdiction of the USA that receive and deliver that information to the client (e.g., without limitation, client-side processing and transmission networks in the USA). When this application is prosecuted or patented under a jurisdiction other than the USA, then "USA" in the foregoing should be replaced with the pertinent country or countries or legal organization(s) having enforceable patent infringement jurisdiction over the present application, and "35 USC § 112 (6)" should be replaced with the closest corresponding statute in the patent laws of such pertinent country or countries or legal organization(s).

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC § 112 (1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" claim limitation implies that the broadest initial search on 112(6) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112 (6) when such corresponding structures are not explicitly disclosed in the foregoing patent specification. Therefore, for any invention element(s)/structure(s) corresponding to functional claim limitation(s), in the below claims interpreted under 35 USC § 112 (6), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112 (6) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any $3^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112 (6), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative methods of implementing data transfers according to the present invention will be apparent to those skilled in the art. Various aspects of the invention have been described above by way of illustration, and the specific embodiments disclosed are not intended to limit the invention to the particular forms disclosed. The particular implementation of the data transfers may vary depending upon the particular context or application. By way of example, and not limitation, the data transfers described in the foregoing were principally directed to medical data implementations; however, similar techniques may instead be applied to any other kinds of data, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims. The following claims are hereby incorporated into the detailed description, with each claim standing on its own as a separate embodiment.

What is claimed is:

1. A method, performed by a first and a second computer, for exchanging medical data, the method comprising:
    at the first computer, generating a first pair of keys including a first private key and a first public key;
    at the first computer, hashing the first public key to generate a first block chain address associated with a first entity;
    at the second computer, generating a second pair of keys including a second private key and a second public key;
    at the second computer, hashing the second public key to generate a second block chain address associated with a second entity;
    at the first computer, linking said first block chain address to first health-care related data, wherein the first health-care related data is stored in a health-care related data repository;
    at the first computer, associating said first health-care related data with said second entity by sending a first block chain transaction to at least one computing device over a network, wherein the first block chain transaction is addressed from said first block chain address to said second block chain address; and
    at the at least one computing device, recording the first block chain transaction in a public ledger, including the first block chain address and the second block chain address, wherein the recording comprises, at each peer in a peer-to-peer network, verifying validity of the public ledger.

2. The method of claim 1, further comprising encrypting, by said at least one first entity, said first health-care related data linked to said at least first block chain address.

3. The method of claim 2, further comprising:
    generating, by a third entity, a third block chain address associated with said third entity;
    requesting access to said encrypted first health-care related data, by said third entity, via said third block chain address, by sending a second block chain transaction from said second entity via said second block chain address; and
    responsive to receiving said request from said at least one third entity, sending, by said second entity, a third block chain transaction from said second block chain address to said third digital block chain address, thereby authorizing, by said second entity, access to said encrypted first health-care related data to said third entity.

4. The method of claim 3, further comprising:
    responsive to said sending, by said second entity, said third block chain transaction from said second block chain address to said third block chain address, granting, by said health-care related data repository, access to said encrypted first health-care related data to said third entity.

5. The method of claim 4, further comprising:
    responsive to said authorizing, by said second entity, access to said encrypted first health-care related data to said third entity, providing payment, by said third entity, to at least one of said second entity and a provider of said health-care related data repository in return for said granted access.

6. The method of claim 1, where wherein said first stored health-care related data comprises at least one of text, at least one image, at least one video clip, at least one audio clip, at least part of at least one genetic sequence and at least one digital file.

7. The method of claim 1, wherein said first stored health-care related data comprises at least a fourth block chain address linked to second stored health-care related data.

8. The method of claim 1, wherein said at least first block chain address or currency transaction includes a hash of at least part of said first stored health-care related data.

9. The method of claim 1, wherein said first entity is a health-care provider of said second entity.

10. The method of claim 3, wherein said first block chain transaction is stored in at least one of a blockchain publicly accessible blockchain and a blockchain accessible to a predefined group of entities, said predefined group of entities comprising at least said first, second and third entities.

11. The method of claim 1, wherein said first block chain transaction comprises at least a description of said first stored health-care related data.

12. A block chain-type digital wallet-based system for exchanging medical data comprising:
    at least one non-transitory computer-readable medium containing computer program instructions executable by at least one computer to perform functions of:
        at a first computer, generating a first pair of keys including a first private key and a first public key;
        at the first computer, hashing the first public key to generate a first block chain address associated with a first entity;
        at a second computer, generating a second pair of keys including a second private key and a second public key;
        at the second computer, hashing the second public key to generate a second block chain address associated with a second entity;
    at the first computer, linking said first block chain address to first health-care related data, wherein said first health-care related data is stored in a health-care related data repository;
    at the first computer, associating said first health-care related data with said second entity by sending a first block chain transaction to at least one computing device over a network, wherein the first block chain transaction is addressed from said first block chain address to said second block chain address; and
    at the at least one computing device, recording the first block chain transaction in a public ledger, including the first block chain address and the second block chain address, wherein the recording comprises, at each peer in a peer-to-peer network, verifying validity of the public ledger.

13. The block chain-type digital wallet-based system of claim 12, wherein the computer program instructions are further executable to perform a function of communicating with said health-care related data repository and encrypting said first health-care related data linked to said first block-chain address.

14. The block chain-type digital wallet-based system of claim 13, wherein generating the first pair of keys comprises generating a third block chain address and depositing said third block chain address in a third digital wallet associated with a third entity.

15. The block chain-type digital wallet-based system of claim 14, wherein the computer program instructions are further executable to perform functions of:

facilitating requesting, by said third entity via said third block chain address, from said second entity via said second digital currency address, access to said encrypted first health-care related data; and responsive to receiving said request from said third entity, facilitating sending, by said second entity, a second block chain transaction from said block chain address to said third block chain address, thereby authorizing, by said second entity, access to said encrypted first health-care related data to said third entity.

16. The block chain-type digital wallet-based system of claim 15, wherein said health-care related data repository is also operable, responsive to said sending, by said second entity, said first block chain transaction from said second digital currency address to said third block chain address, for granting access to said encrypted first health-care related data to said third entity.

17. The block chain-type digital wallet-based system of claim 15, wherein the computer program instructions are further responsive to said authorizing, by said second entity, access to said encrypted first health-care related data to said third entity, to perform a function of providing payment by said third entity to at least one of said second entity and a provider of said health-care related data repository in return for said granted access.

18. The block chain-type digital wallet-based system of claim 12, wherein said first stored health-care related data comprises at least one of text, at least one image, at least one video clip, at least one audio clip, at least part of at least one genetic sequence and at least one digital file.

19. The block chain-type digital wallet-based system of claim 12, wherein said first stored health-care related data comprises a fourth block chain address linked to second stored health-care related data.

20. The block chain-type digital wallet-based system of claim 12, wherein said first block chain address includes a hash of at least part of said first stored health-care related data.

21. The block chain-type digital wallet-based system of claim 12, wherein said first entity is a health-care provider or health care device or machine of said second entity.

22. The block chain-type digital wallet-based system of claim 12, wherein said first block chain transaction is stored in at least one of a digital-currency publicly accessible blockchain and a digital-currency blockchain accessible to a predefined group of entities, said predefined group of entities comprising at least said first, second and third entities.

23. The block chain-type digital wallet-based system of claim 12, wherein said first block chain transaction comprises at least a description of said first stored health-care related data.

\* \* \* \* \*